United States Patent [19]
Toll

[11] Patent Number: 4,588,380
[45] Date of Patent: May 13, 1986

[54] ORTHODONTIC APPLIANCE

[76] Inventor: Douglas E. Toll, Kronberger Str. 10, 6232 Bad Soden/Taunus Postfach 1504, Fed. Rep. of Germany

[21] Appl. No.: 631,279

[22] Filed: Jul. 16, 1984

Related U.S. Application Data

[63] Continuation-in-part of Ser. No. 421,800, Sep. 23, 1982, abandoned.

[51] Int. Cl.⁴ .............................................. A61C 7/00
[52] U.S. Cl. ......................................................... 433/5
[58] Field of Search ............................................ 433/5

[56] References Cited

U.S. PATENT DOCUMENTS 4,087,915 5/1978 Andrews ................................ 433/5
4,184,254 1/1980 Kraus .................................... 433/15

FOREIGN PATENT DOCUMENTS 667040 10/1938 Fed. Rep. of Germany ........ 433/17

*Primary Examiner*—Robert Peshock
*Attorney, Agent, or Firm*—Freilich, Hornbaker, Rosen & Fernandez

[57] ABSTRACT

An improved orthodontic appliance of the type generally referred to as headgear, for applying a force to a tooth to move the tooth bodily and/or rotationally, and for pushing outward the cheek to encourage spontaneous jaw growth. The appliance comprises an outer bow intended to be retained adjacent the user's face by a neck strap and an inner bow attached to the outer bow intended to fit within the user's mouth proximate to his cheeks. The inner bow includes left and right activating arms, which arms include shoulder portions to push the cheeks outwardly, and which arms also include noncircular engagement means adapted to fit snugly within tubes fixed to a left and a right rear tooth. The activating arms are formable and sufficiently resilient that they can be selectively deformed to apply a force to the teeth to achieve the desired movement. The noncircular engagement means prevents undesired rotational movement between the appliance and the teeth, and assures that the force developed by the arms will be properly transferred to the teeth.

3 Claims, 6 Drawing Figures

ORTHODONTIC APPLIANCE

This is a continuation-in-part of application Ser. No. 06/421,800 filed Sept. 23, 1982 and now abandoned.

FIELD OF THE INVENTION

This invention relates generally to improvements in orthodontic appliances which use both an intra-oral device such as an inner bow and an extra-oral device such as a neck or head strap for moving teeth.

BACKGROUND OF THE INVENTION

Orthodontic appliances, or headgear, for applying a force to a tooth are well known. Such applicances typically comprise a spring steel wire member having an outer bow and an inner bow. The left and right activating arms of the inner bow are inserted into a user's mouth and the distal end of each is inserted into a tube affixed to a tooth. In use, each inner bow arm is adjusted so as to impart a force tending to move the tooth in a desired manner. The distal end of each inner bow arm and its tube are typically of circular cross section thus allowing rotational movement relative to one another making it difficult to achieve certain precisely controlled tooth movements, and impossible to achieve certain others.

SUMMARY OF THE INVENTION

The present invention is directed to an improved orthodontic appliance using both an intra-oral device (i.e., inner bow) and an extra-oral device (e.g., head strap) for more precisely controlling tooth movement.

In accordance with an important aspect of the invention, the distal ends of the inner bow are dimensioned to be snugly and removably received in recesses formed in members anchored to left and right rear teeth. The inner bow ends and recesses are configured to prevent any relative rotational movement therebetween to thereby enable forces produced by the inner bow to be applied more directly to the teeth.

In accordance with a first embodiment, each inner bow end is bent back upon itself to form a noncircular cross section receivable in a similarly shaped and dimensioned recess of a tubular member anchored to a rear tooth.

In accordance with a second embodiment, each inner bow end is bifurcated to thus form a noncircular engagement means for insertion into a suitably configured tube affixed to a user's tooth.

In accordance wth a further aspect of the invention, left and right side portions of the inner bow are tilted outwardly to push the cheek away from the user's teeth.

The utilization of an extra-oral appliance together with an inner bow configured in accordance with the invention enables a tooth to be more effectively moved than has heretofore been possible. Thus a tooth can be bodily moved distally (rearward) or buccally (outward) or superiorly (upward). Concurrently it can be torqued (around a horizontal axis) and/or rotated (around a vertical axis).

DESCRIPTION OF THE PREFERRED EMBODIMENT

Figures 1, 2:
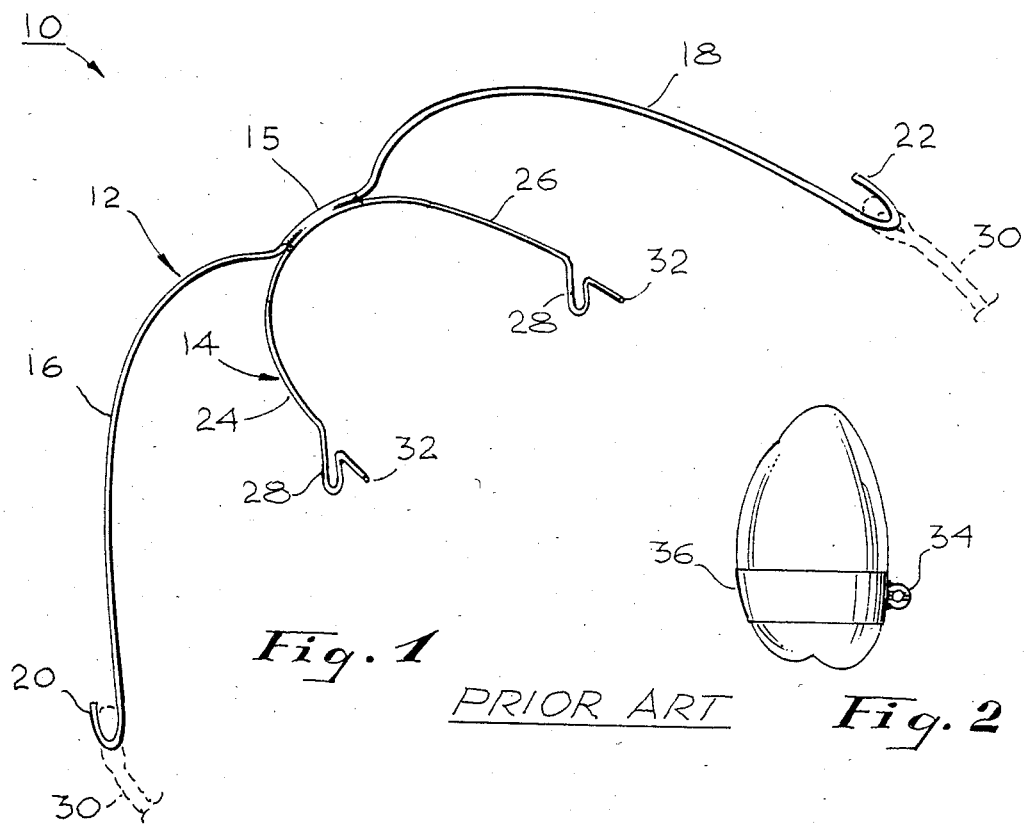
FIG. 1 is an isometric view depicting a typical prior art orthodontic appliance.
FIG. 2 is an end view of a portion of the appliance of FIG. 1 showing the distal end of the inner bow within a tube affixed to a tooth.

Attention is initially directed to FIG. 1 which illustrates a conventional orthodontic appliance 10 of the headgear type which includes both an intra-oral inner bow and an extra-oral outer bow and neck or headstrap. More particularly, the appliance 10 is comprised of an outer bow 12 and an inner bow 14, both preferably formed of spring steel wire, and connected, as by a solder joint at 15.

The outer bow 12 includes left and right arms 16 and 18 respectively terminating in hooks 20 and 22. The inner bow 14 includes left and right activating arms 24 and 26. Each arm 24, 26 typically includes a short loop 28 to facilitate manually orienting the arm ends. The inner bow arms 24, 26 are typically of circular cross section and of a diameter which enables them to be readily manually deformed by an orthodontist. The arms 24, 26 are sufficiently resilient to enable each to apply a sustained force to a tooth sufficient to move it.

More particularly, in use of the appliance 10 of FIG. 1, the inner bow 14 is inserted into a user's mouth and a neck or head strap 30 is connected to outer bow hooks 20, 22 to hold the arms 16, 18 adjacent the user's face with the inner bow 14 at a fixed position within the user's mouth. The distal end 32 of each of the inner bow arms 24, 26, is inserted by the user into a tube 34 affixed to the tooth to be moved. The tube 34 can be directly bonded to the tooth or affixed to a band 36 which encircles the tooth. As is depicted in FIGS. 1 and 2, the distal end 32 of each inner bow arm is typically of circular cross section, as is the recess in tube 34. As a consequence, the end of each arm 24, 26 can rotate within its tube 34 thereby preventing the force developed by the arm from being accurately transferred to the tooth. Thus, it is impossible to achieve precisely controlled tooth movement.

The improved extra-oral orthodontic appliance in accordance with the present invention more directly couples a force developed by the appliance inner bow to selected left and right rear teeth in order to achieve more precisely controlled tooth movement. An extra-oral appliance having an inner bow configured in accordance with the invention can readily produce bodily movement either distally (rearward) or buccally (outward) or superiorly (upward) and additionally, can selectively torque a tooth around orthogonal horizontal axes and/or rotate it around a vertical axis. Controlled motion of this sort has not previously been achievable with patient removable appliances.

Figures 3, 4:
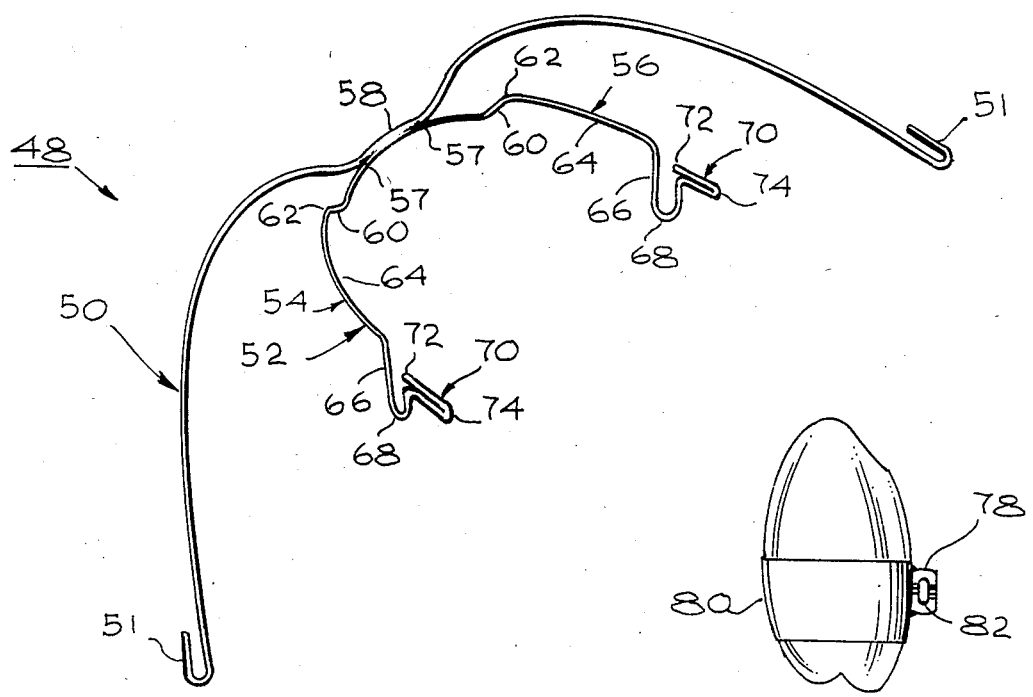
FIG. 3 is an isometric view of an orthodontic appliance in accordance with a first embodiment of the invention including an improved inner bow.
FIG. 4 is an end view depicting the noncircular bow end of FIG. 3 fitted within a receiving member of like cross section affixed to a tooth.

Attention is now directed to FIG. 3 which illustrates a first embodiment of an orthodontic appliance 48 in accordance with the present invention. The orthodontic appliance 48 of FIG. 3 includes an outer bow 50, having end hooks 51, substantially identical to the aforediscussed outer bow 12, and an inner bow 52 for insertion in the user's mouth. The inner bow 52 is comprised of left and right activating arms 54 and 56 each having a proximal end 57 soldered to the outer bow and a free distal end 70. Each arm includes multiple bends between its proximal and distal ends. Thus, extending from solder joint 58 at the junction with the outer bow, arms 54, 56 includes a first upwards bend 60, and then a lateral bend 62 to a substantially straight shoulder portion 64. The portion 64 extends to a downward bend 66 which preceeds substantially 180° loop 68. After the loop 68, the arms terminate in a distal end 70.

Each distal end 70 is preferably formed by bending a short section 72 of the wire back upon itself at 74 soldering the parallel portions to thereby form a noncircular substantially oval cross section.

As depicted in FIG. 4, a tube 78 affixed to the tooth, either by direct bonding or by a band 80 encircling the tooth, includes a passage 82 of noncircular cross section conforming to the cross section of the distal end 70 of the inner bows arms 54, 56. The distal end 70 is dimensioned to fit snugly within the passage 82.

In the use of the improved orthodontic appliance 48 in accordance with the invention, the user will wear it in substantially the same manner as was discussed in connection with FIG. 1. That is, a strap will typically be attached to the outer bow hooks 51 to support the outer bow arms adjacent the user's face and fix the position of the inner bow within the mouth. The inner bow arms 54, 56 will extend into the vestibule between the user's bone and inner cheek with the long shoulder portion 64 tilted slightly outward tending to push the cheek away from several teeth forward of the tooth to which the tubes 78 are affixed. The distal ends of the arms 54 and 56 are inserted within the tubes 78. The orthodontist will typically adjust the resilient arms 54, 56 in a manner which applies a force to the tooth to move the tooth in the desired direction, either bodily or rotationally. By utilizing inner bow arms having a distal end with a noncircular cross section, the force developed by each arm will be accurately transferred to the tooth thereby achieving very precisely controlled tooth movement.

Figure 5:
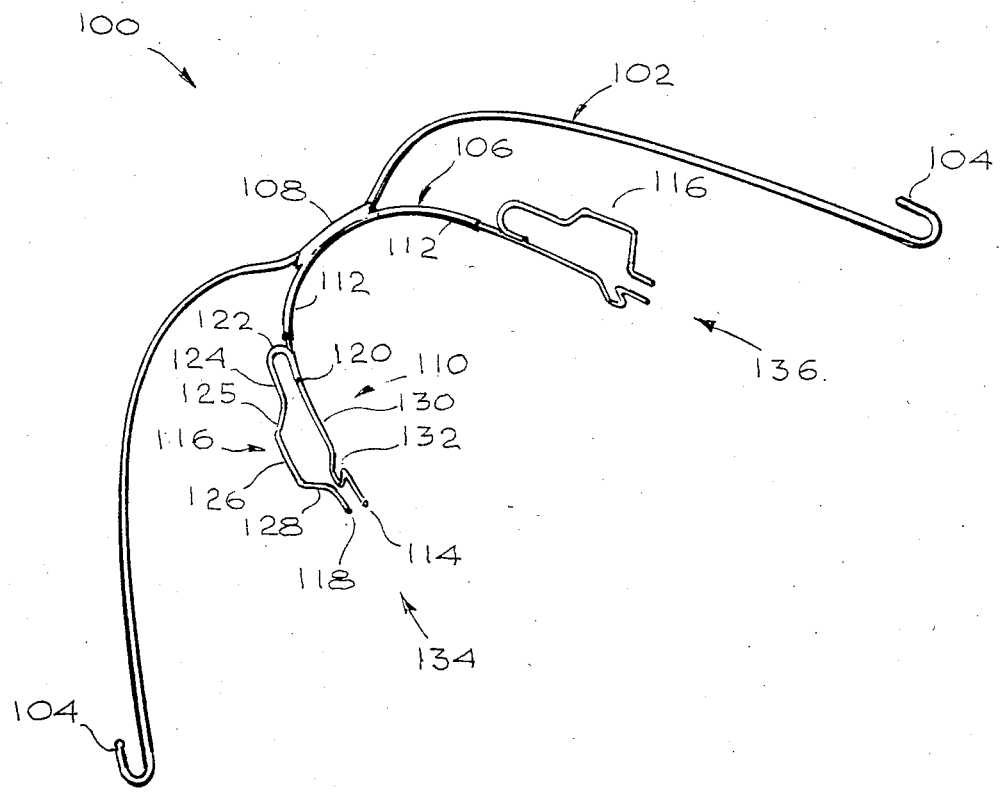
FIG. 5 is an isometric view of a second embodiment of an orthodontic appliance in accordance with the invention including an improved inner bow employing spaced arm ends to create a noncircular engagement means.

Attention is now directed to FIG. 5 which illustrates an alternative embodiment of extra-oral orthodontic appliance 100 in accordance with the present invention.

Since the appliance 100 is symmetrical about a longitudinally extending vertical plane, corresponding elements sometimes will be identified with the same reference numeral. Thus, the improved appliance 100 includes an outer bow 102, having end hooks 104, substantially identical to the aforementioned outer bow 12. The appliance 100 also includes an inner bow 106 for insertion in a user's mouth. The inner bow 106 is rigidly affixed to the outer bow 102 by means of a solder joint at the center portion 108 of the outer bow 102, which center portion 108 also defines the center portion of the inner bow 106. The distal ends of the inner bow 106 are bifurcated as will be discussed hereinafter to define engagement means 110 for cooperating with tubes anchored to a user's left and right rear teeth. The engagement means 110 includes, in the preferred embodiment, left and right lower arms 112 which each extend substantially rearwardly from the inner bow center portion 108 to a free distal end 114. The engagement means 110 also includes left and right upper arms 116, each of which extends substantially rearwardly from a point on said respective left or right lower arm 112 mediate the inner bow center portion 108 and the free distal end 114 of the respective lower arm 112, to a free distal end 118.

More particularly, each of the upper arms 116 includes multiple bends between its forward and rearward ends. Thus, extending forward from a solder joint 120, the upper arm 116 includes a first upwards bend 122 to a rearward extending, substantially straight, first shoulder portion 124. The shoulder portion 124 extends to a second upwards bend 125, which in turn extends to a rearwardly extending, substantially straight, second shoulder portion 126. The shoulder portion 126 extends to a downwards bend 128 which precedes the horizontal, rearwardly extending, free distal end 118.

Each of the lower arms 112 of the engagement means 110 includes a horizontal, substantially rearwardly extending portion 130, a substantially 180°, downward extending loop 132, and the horizontal, rearwardly extending, free distal end 114. Lower distal ends 114 are parallel to and in spaced-apart relationship with respect to upper distal ends 118. It is to be noted that the lower arms 112 are preferably formed by a tubular center portion 108 which defines a central passage for telescopically receiving forwardly projecting ends of elements 130 which are initially adjustably positioned and then fixed by soldering or by crimping tube 108.

In accordance with a significant aspect of the preferred embodiment, the engagement means 110 includes a left portion 134 comprised of the left lower arm 112 and the left upper arm 116, and a right portion 136 comprised of the right lower arm 112 and the right upper arm 116.

Figure 6:
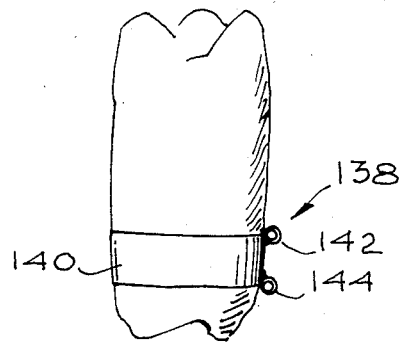
FIG. 6 is an end view of the appliance depicted in FIG. 5 showing the inner bow arm ends received in spaced tubes affixed to a tooth.

As depicted in FIG. 6, receiving means 138, affixed to a tooth either by direct bonding or by a band 140 encircling the tooth, includes upper and lower tubes 142 and 144 having internal passages of circular cross section conforming to the cross sections of upper and lower distal ends 118 and 114, and adapted for snugly receiving said distal ends.

In the use of the improved orthodontic appliance 100, the user will wear it in substantially the same manner as was discussed in connection with FIG. 1. That is, a neck strap or highpull will be attached to the outer bow hooks 104 to support the outer bow arms adjacent the user's face and fix the position of the inner bow within the mouth. The four inner bow arms 112 and 116 will extend into the vestibule between the user's bone and inner cheek with the shoulder portions 124 and 126 tilted slightly outward tending to push the cheek away from the teeth forward of the teeth to which the receiving means 138 is attached. This allows, according to the Frankel effect, for the spontaneous outward (buccal) growth of the jaw by removing the constant inward pressure of the cheeks.

Distal ends 114 and 118 are removably inserted into corresponding passages in the tubes 142 and 144 of the receiving means 138. The orthodontist will typically form the resilient arms 112 and 116 to cause the application of a force to the teeth in a desired direction. Because the arms 112 and 116 are relatively long, it makes it possible for the appliance 100 not only to cause buccal root torque and/or buccal body movement, but to actually cause a torsion or yaw of the anchoring teeth. This allows a different movement to take place in the root portion of the tooth than on the crown portion. This means that for the first time a tooth can be moved more towards the cheek on the root end than on the chewing surface. This also means that the rear occlusial (chewing) side of the tooth can be moved up more than the cheek side of the tooth. The fact that the two distal ends on each side of the inner bow are relatively far apart and anchored to the same tooth permits the tooth to be torqued or rotated around three perpendicular X, Y, and Z axes simultaneously. This capability to effect a so-called "twisting movement" can frequently be used to more quickly, stably, and efficiently correct orthodontic problems.

This twisting movement together with the use of upper and lower arms to achieve a large holding off or bumper effect against the cheeks enables both the upper and lower jaws to simultaneously grow.

In summary, the appliance 100, which can be readily removed and reinserted by the patient, provides for upward, backward, outward, and rotational tooth movements. With the greatly increased surface defined by the inner bow upper and lower arms to hold off the cheeks, the resulting increasing jaw size permits desired tooth movement to be readily accomplished.

I claim:

1. An orthodontic appliance including an inner bow intended to be received in a user's mouth, an outer bow intended to extend around the user's face and having a center portion affixed to a center portion of said inner bow, and a strap connected to the ends of said outer bow intended to engage the user's head to pull said outer bow to precisely move first and second rear teeth of the user;

said inner bow being formed of manually deformable spring wire material and including first and second arms each extending substantially rearwardly from said inner bow center portion to a free distal end;

each of said first and second arm distal ends having a noncircular cross section;

first and second tubular members respectively secured to said first and second rear teeth, said tubular members defining internal passageways of noncircular cross section for respectively snugly receiving the distal ends of said first and second arms to enable said teeth to be precisely bodily moved; and means formed on each of said first and second arms between said inner bow center portion and the arm's distal end displaced outwardly from, and elongated along, a line substantially conforming to the user's jaw for engaging the inner side of the user's cheek to hold the cheek away from at least some of the teeth between the user's front teeth and said first and second rear teeth.

2. The appliance of claim 1 wherein said inner bow distal ends of noncircular cross section are formed by bending the wire material thereof back upon itself.

3. An orthodontic appliance including an inner bow intended to be received in a user's mouth, an outer bow intended to extend around the user's face and having a center portion affixed to a center portion of said inner bow, and a strap connected to the ends of said outer bow intended to engage the user's head to pull said outer bow to precisely move left and right rear teeth of the user;

said inner bow being formed of manually deformable spring wire material and including left and right engagement means;

said left and right engagement means each defining a noncircular cross section;

left and right receiving means respectively secured to said left and right rear teeth, said receiving means defining internal passageways for respectively snugly receiving said left and right engagement means to enable said teeth to be precisely bodily moved or three-dimensionally rotated;

said left and right engagement means comprising:

left and right lower arms, each lower arm extending substantially rearwardly from said inner bow center portion to a free distal end;

left and right upper arms, each upper arm extending substantially rearwardly from a point on said respective left or right lower arm mediate said inner bow center portion and said free distal end of said respective lower arm, to a free distal end; and wherein said left and right receiving means comprise left and right upper and lower tubular members defining internal passageways for respectively snugly receiving the free distal ends of said left and right lower and upper arms;

each of said left and right engagement means including a portion displaced outwardly from, and elongated along, a line substantially conforming to the user's jaw for engaging the inner side of the user's cheek to hold the cheek away from at least some of the teeth between the user's front teeth and said left and right rear teeth.

* * * * *